(12) United States Patent
Wang et al.

(10) Patent No.: US 11,357,919 B2
(45) Date of Patent: Jun. 14, 2022

(54) OPTICAL SYSTEM AND A SUPPLEMENTAL DATA COLLECTING DEVICE FOR A MEDICAMENT DELIVERY DEVICE, THE MEDICAMENT DELIVERY DEVICE ASSEMBLY AND A METHOD

(71) Applicant: SHL Medical AG, Zug (CH)

(72) Inventors: Yung-Han Wang, Taipei (CN); Chih-Shuen Lin, Taipei (CN)

(73) Assignee: SHL MEDICAL AG, Zug (CH)

( * ) Notice: Subject to any disclaimer, the term of this patent is extended or adjusted under 35 U.S.C. 154(b) by 468 days.

(21) Appl. No.: 16/378,218

(22) Filed: Apr. 8, 2019

(65) Prior Publication Data
US 2019/0307965 A1   Oct. 10, 2019

(30) Foreign Application Priority Data
Apr. 9, 2018   (EP) ..................................... 18166373

(51) Int. Cl.
*A61M 5/315*   (2006.01)
*A61M 5/24*   (2006.01)
*A61M 5/31*   (2006.01)

(52) U.S. Cl.
CPC .......... *A61M 5/31525* (2013.01); *A61M 5/24* (2013.01); *A61M 5/31545* (2013.01);
(Continued)

(58) Field of Classification Search
CPC .......... A61M 5/31525; A61M 5/31545; A61M 2005/3126
See application file for complete search history.

(56) References Cited

U.S. PATENT DOCUMENTS

2008/0287865 A1* 11/2008 Nielsen ............. A61M 5/31556
604/65
2014/0330215 A1* 11/2014 Kikuchi ................. A61M 5/24
604/189
(Continued)

FOREIGN PATENT DOCUMENTS

KR   20170105236 A   9/2017
WO   2011117212 A1   9/2011
(Continued)

OTHER PUBLICATIONS

European Search Report issued in European Application No. 18166373 dated Jun. 15, 2018.
(Continued)

*Primary Examiner* — Dung T Ulsh
(74) *Attorney, Agent, or Firm* — McDonnell Boehnen Hulbert & Berghoff LLP (57) ABSTRACT

A medicament delivery device for injections or inhalations comprises a supplementary device affixed to it. The supplemental device is provided with an optical system for monitoring a dosage of medicament. The optical system is able to receive reflected and refracted optical images of the dosage value as the optical signals from the medicament delivery device and thus keep a dosage window on the medicament delivery device free for direct monitoring by a user due to changing the transferring of the optical signal direction. The supplemental device is able to analyze, record and display the dosage and the other relevant data on a display and inform the user. The supplemental device is also able to transmit the medicament delivery data to an external device. A method for collecting the medicament delivery data including the medicament dosage information from a dosage setting mechanism and controlling the dosage, recording and displaying the dosage data by the supplemental device on its display is disclosed. The method allows due to changing of
(Continued)

the optical signal transmitting direction by the optical system also simultaneously monitoring the dosage window of the medicament delivery device. This method increases a safety and minimizes the dosage setting errors.

17 Claims, 6 Drawing Sheets

(52) U.S. Cl.
CPC .... *A61M 5/31553* (2013.01); *A61M 5/31585* (2013.01); *A61M 2005/3126* (2013.01)

(56) References Cited

U.S. PATENT DOCUMENTS

| | | | |
|---|---|---|---|
| 2015/0202375 A1* | 7/2015 | Schabbach | G16H 20/17 604/207 |
| 2017/0182258 A1* | 6/2017 | Michael | A61M 5/31568 |
| 2017/0304545 A1 | 10/2017 | Blei et al. | |

FOREIGN PATENT DOCUMENTS

| | | |
|---|---|---|
| WO | 2013004843 A1 | 1/2013 |
| WO | 2013055401 A1 | 4/2013 |
| WO | 2016075122 A1 | 5/2016 |

OTHER PUBLICATIONS

English Translation of Abstract of Korean Patent Application No. 20170105236 dated Mar. 20, 2019.

\* cited by examiner

OPTICAL SYSTEM AND A SUPPLEMENTAL DATA COLLECTING DEVICE FOR A MEDICAMENT DELIVERY DEVICE, THE MEDICAMENT DELIVERY DEVICE ASSEMBLY AND A METHOD

CROSS REFERENCE TO RELATED APPLICATIONS

The present application claims priority to European Patent Application No. 18166373.3 filed on Apr. 9, 2018. The entire disclosure contents of these applications are hereby incorporated by reference into the present application.

TECHNICAL AREA

The present invention relates to a supplementary device for use with a medicament delivery device of a pen-type injector or an inhalator, an optical system and a method for collecting data related to a medicament dosage information from a dosage setting device, recording and displaying the dosage data by the supplemental device.

BACKGROUND OF INVENTION

There is a variety of diseases which require regular treatment by injection or inhalation of a medicament. Often such treatments are performed by patients themselves, sometimes once or several times a day. Many devices on the market for self-administering doses of medicament are provided with dose setting features or mechanism. Problem arises when a patient does not keep a record of which medicament, which dosage and how often it is administrated.

A number of supplemental devices that are used to record information about various times the medicament is to be administrated, quantity and other parameters are known on the market.

WO2013/055401 discloses a supplementary device for attachment to a drug injection device for monitoring injection doses and having optical character recognition imaging system using a camera, a plurality of light sources and a processor that activates a plurality of light sources and receives multiple images captured by the camera combining those into a single image.

US 2017/0304545 discloses an apparatus for determining information associated with reflection characteristics when optically reading data. The apparatus uses a light concentrator concentrating light form an illumination source, an optical sensor receiving the image and a processor using the sensor output signal.

It might be difficult for older patients to see a correct medicament dosage setting in an indicator window and therefore, there were developed devices that by optical sensors capture images of a dosage indicator and record those or transmit images on a bigger display or screen.

WO2016/075122 discloses a medicament dosage data collection device which captures images of a dosage indicator of a medicament delivery device, and if injection is administrated without a dose setting, prompts the user to set a value for storing in a dosage log. The data collection device uses optical character recognition, optical patters recognition and determination of direction of rotation if a dosage component. In the known supplementary devices, the optical information sensors for capturing and recording images are usually situated just in front of the medicament delivery dosage setting window so that the only these sensors situated opposite the dosage window are able to receive information and the user cannot see the dosage by his/her eyes directly from the dosage window. This however, may lead to inaccurate dosing as any processing faults of the supplemental device will be forwarded to the user interface.

However, with a direct view of the dosing scale of the medicament delivery device, even having a supplementary device for dosage monitoring and an injections or inhalations log recording, the user can be more certain about the selected dose for each time Further, a supplementary device display that is rapidly updated to show current dose settings, requires more power consumption leading to a need of more powerful, bigger heavier, battery. The display screen itself might also require extra space that might increase the supplementary device dimensions and weight which is not desired. Therefore, it might be advantageous to avoid having the supplemental device display and transmit the medicament delivery data to another external device with a user interface and/or apply a software that avoids this need.

There is a need to have the supplementary device that might show a time elapsed since the last injection or inhalation had been performed by the medicament delivery device, and then remind the user about the necessary repetition of the injection or inhalation. It might also collect all medical information such as e.g. dosage, a medicament type and e.g. blood glycose changes for a doctor reference. This information might be saved in a memory (as a separate unit or integrated) and if/when necessary to be transferred or transmitted to a smart phone, computer, cloud or an accessory device via wireless communication, such as Bluetooth.

It is also desired to overcome the other disadvantages of the known supplementary devices for the medicament delivery device such as auto-injectors, pen-injectors and inhalators where the user need to set a dose himself and shall have a possibility to monitor it directly during setting.

BRIEF DESCRIPTION OF INVENTION

The supplemental device according to the invention comprises an optical system which is able optically capture the dosage value images and transmitting those images of the dosage values for recording and/or processing by a processor. The taken dosage values might be recorded in the dosage log and, if desired, transmitted on a display of the supplemental device for the user convenience. The optical system allows the user see and control the dosage values displayed in the dosage window of a medicament delivery device itself without dismounting of the supplemental device away from the medicament delivery device for a possible manual adjustment of the medicament dosage. As the user can directly recognise the dosage value digits, the dosage precision is the highest possible.

As the user still reads the actual dosage from the medicament dosage window directly on the pen-injector, the auto-injector or the inhalator even when the supplemental device is attached, any temporary error or abnormality in the supplemental device functioning would not affect the user for taking a wrong dosage, and in any circumstances, the correct dosage will be injected or inhaled even if the supplemental device fails. This increases the safety of usage of the supplemental device. Besides that, the supplemental device would not affect the users' possibility to rotate a dosage knob for setting or change a dose.

These and other aspects of, and advantages with, the present invention will become apparent from the following detailed description of the invention and from the accompanying drawings.

According to one of the aspect of the invention, there is an optical system for monitoring a dosage setting for an injection or inhalation by a dosage setting mechanism for a medicament delivery device. The dosage setting mechanism comprises a dose indicator for example such as a dose drum or the like with dosage values indications on its surface. A dosage opening or a dosage monitoring window is made on a medicament delivery device housing circumferential outer surface, surrounding the dose indicator. The dosage value indications are displayed through the dosage opening. The optical system comprising components such as an optical sensor having an optical axis B for sensing an optical signal of the dosage value indications transmitted along the optical axis B. There is at least one optical element for receiving the reflected optical signal of the dosage value indications from the dosage opening for transmitting to and detecting by the optical sensor. The optical system components such as the optical sensor and at least one of the optical element might be situated adjacently on the outer surface of the medicament delivery device housing on a side of the dosage opening or surrounding the dosage opening so that to leave the dosage opening area free for enabling a user to view the dosage value indications displayed on the dosage indicator in the dosage opening.

The optical element might be at least one of a half-silvered mirror, a convex mirror, a combination of a convex lens and a mirror for capturing a reflected optical signal of the dosage value indications from the dosage opening and able to change a direction of the optical signal between the dosage opening and the optical sensor. The optical sensor might be one of a camera with an integrated lens or without the lens, a mouse sensor and a combination of a camera and a lens.

The optical system might comprise a light source for illuminating the dosage value indications displayed by the dose indicator in the dosage opening.

In a first embodiment of the invention, a longitudinal axis of the elongated tubular medicament delivery device and an optical axis of the optical sensor are positioned co-axially, the optical sensor is spaced adjacent to the dosage opening of the medicament delivery device on a first side of the dosage opening. At least one the optical element is spaced on an opposite side of the dosage opening so that the optical signal reflected from the dosage opening is received by the optical element and transmitted to the optical sensor along its optical axis.

In a second embodiment of the invention, the optical sensor has its optical axis positioned orthogonally to the medicament delivery device longitudinal axis. The optical sensor might be spaced adjacent to the dosage opening of the medicament delivery device on a first side of the dosage opening and a convex mirror might be situated on a second side of the dosage opening so that the optical signal reflected from the dosage opening is received by the convex mirror, refracted and transmitted to the optical sensor.

Alternatively, the optical sensor has its optical axis positioned orthogonally to the medicament delivery device axis. The optical sensor, a mirror and a convex lens might be situated on the same side of the dosage opening so that the optical signal from the dosage opening is received by the convex lens, refracted and transmitted via the mirror to the optical sensor.

The optical sensor is for example one of the optical sensor able to transform the optical signal into an electrical signal, the mouse sensor able to measure a distance between two positions of the dose indicator when setting the dosage value creating a signal and an optical camera able to take photos of digits and line marks on the dose indicator corresponding to the dosage value indications displayed through the dosage opening providing optical signals wherein the optical sensor is able to transmit the signals for processing, analysing and storage.

A light source for illuminating the dosage value indications enabling to see those might be a surrounding light or a separate light source or a light source integrated in the optical sensor or the camera.

According to a second aspect of the invention, there is a supplemental device comprising a housing and the optical system as disclosed above. The supplemental device is to be used together with a medicament delivery device and adapted for collecting and recording medicament delivery data from the medicament delivery device. The medicament delivery device has a dosage setting mechanism and a dosage value indications viewing window or opening situated on a circumference surface of the medicament delivery device housing. The supplemental device further comprises a sound sensor detecting for example a rotational sound of the dose setting mechanism, e.g. such as a dose drum. A processing unit is arranged for processing the output signal from the optical sensor. The sound sensor is adapted to activate the processing unit when the dosage setting starts manually by rotation a knob. It might also comprise a memory (e.g. RAM random access memory or another kind of memory), integrated into the processing unit or as a separate unit. The memory unit is arranged for receiving and recording the data from the optical sensor.

A battery (35) is provided as a power supply and a transparent monitoring window is made in the housing for enabling a user to view the dosage value displayed in the dosage opening of the medicament delivery device housing. The supplemental device may further comprise one of an optical display or an electronic paper display for displaying the medicament delivery dosage data transmitted from the processing unit, the data been received from the dosage setting mechanism of the medicament delivery device by the optical sensor, transmitted to and processed by the process unit, the optical display is to be situated visibly on the housing and leaving free space for the transparent monitoring window; a touch panel for activating the processing unit and displaying the dosage value and a combination of the optical display and the touch panel.

The supplemental device is to be firmly and releasably attached to the medicament delivery device circumferential surface of the housing so as the transparent monitoring window of the supplemental device housing is to be situated co-axially and just opposite the dosage monitoring opening of the dosage setting mechanism of the medicament delivery device housing when those are been assembled together. Alternatively, the supplemental device housing might be adapted for releasably receiving the medicament delivery device housing at least partially to be inserted in the supplemental device housing so that the dosage opening of the medicament delivery device housing is situated opposite to the transparent monitoring window of the supplemental device housing.

The sound sensor detects the sound of the dosage setting mechanism movement or e.g. a rotational sound of the dose setting drum might be chosen from one of a microphone, an accelerometer and a vibration sensor.

The supplemental device further may comprise a communication module for communicating and transmitting the dosage data to an external device.

where the external device can be one of a mobile device such as a mobile or cell phone, a computer and a remote server such as a cloud for recording, storage and monitoring of the injection or inhalation medicament delivery data such as a dosage, time of delivery, date, frequency, medicament, etc.

The supplemental device can be provided with a separate or additional memory unit. The supplemental device might further comprise a resetting button (not shown) which enable a manual reset of the supplemental device. Alternatively, after a number of circles of medicament delivery or a predetermined time, the supplemental device can be re-set automatically, if this mode is preferred by a user.

According to a third aspect of the invention, a medicament delivery device having an elongated tubular housing, a dosage setting mechanism with a dose indicator, e.g. such as a dosage setting drum on the housing distal end. The dose indicator has dosage value indications on its surface in form on digits and/or line marks. A dosage monitoring opening, e.g. such as a dosage monitoring window is situated on a circumference surface of the medicament delivery device housing, which encloses the dose indicator so that the dosage value indications on the dose indicator surface are visible through the dosage monitoring opening in the medicament delivery housing. The medicament delivery device comprises also the optical system as disclosed above, which is able to receive and transmit the reflected optical image signal from the dosage indicator, corresponding the dosage value indications visible through the monitoring opening of the medicament delivery housing to another device such as a supplemental device like an accessory or an external remote mobile device like a mobile phone or a computer for processing, recording and storage of the medicament delivery data.

A medicament delivery device assembly comprises an elongated tubular medicament delivery device e.g. a disposal device for a multiple injections and or inhalators of the medicament. The medicament delivery device has a proximate end for medicament delivery and a distal end with a dosage setting mechanism and a supplemental device for monitoring, receiving and recording the injection data located at the distal end of the medicament delivery device where the supplemental device comprises the optical system according to the invention.

According to a fourth aspect of the invention, a method of collecting and recording a medicament delivery data comprising delivery information e.g. about a dosage, time of delivery, frequency, medicament, date, etc. from a medicament delivery device is provided. The medicament delivery device is e.g. of a pen-type injector, an auto-injector or an inhalator has a dosage setting mechanism with a dose indicator, e.g. such as a dose setting drum or the like. The dose indicator has a dosage value indications on its surface and a dosage displaying window or opening on the delivery device circumference surface for displaying the dosage values. The method comprises steps of detecting a sound from a dose indicator movement, e.g. a rotational sound from the dose setting drum or other kind of the setting mechanism by a sound sensor and activating a processing unit by the sound sensor. Then, receiving an optical data of the required chosen dosage value such as a reflection of an optical signal from the dosage opening by at least one optical element, where the optical element is one of a half-silvered mirror, a convex mirror and a combination of a convex lens and a mirror. The optical element transmits the optical signal to the optical sensor, which in its turn, transmits the output signal to a processing unit. The optical data is processed and recorded by the processing unit, saving the optical data in a memory. The method implicates a transmitting of the optical data e.g. the optical image signal, to an optical sensor along its optical axis by changing a direction of the optical data transmission between the dosage opening and the optical sensor by the optical element.

In one possible embodiment of the invention, the optical display of the supplemental device may be omitted at all, and thus the battery size and consequently the supplemental device dimensions can be decreased, if the dosage value data would be transmitting directly to an external unit having a display, such as e.g. a mobile phone or a computer instead of been displayed on the supplemental device.

BRIEF DESCRIPTION OF DRAWINGS

In the following detailed description of the invention, reference will be made to the accompanying drawings, of which

DETAILED DESCRIPTION OF THE INVENTION

In the following description, the wording a medicament delivery device will be used. In this context, the medicament delivery devices may include a number of devices capable of delivering certain doses of medicament to the user, such as e.g. injection devices with or without needles, inhalers of all kinds, such as powder, aerosol driven, gas, nebulizers having mouth or nasal pieces, dispensers for medicament in tablet form etc. In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Figure 1A:
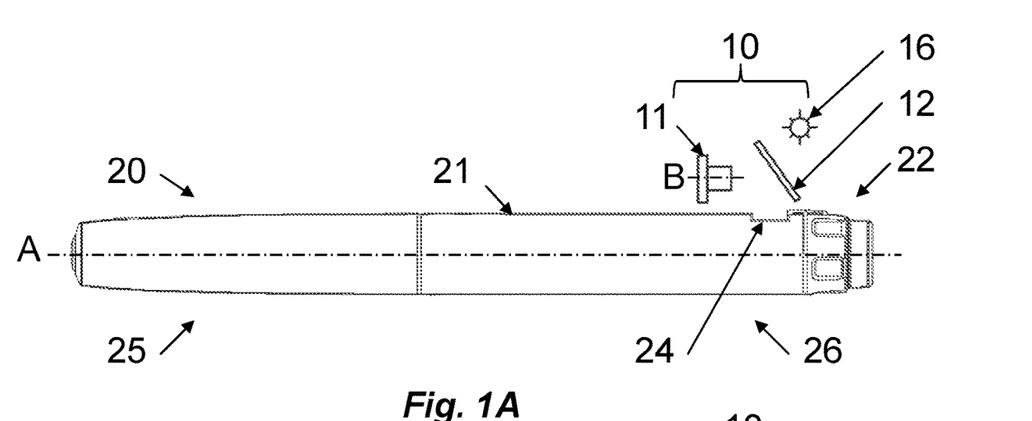
FIG. 1A is a schematic illustration of an optical system for capturing a reflected image of a dosage value visible in a dosage monitoring opening of the dosage setting mechanism by a half-silvered mirror and a camera as an optical sensor.

The first embodiment of the optical system 10 might be used for example in the supplemental device 30 and allowing a direct monitoring of the dosage values displayed during the dosage setting process through the dosage setting window of a medicament delivery device 20 will be disclosed below. The medicament delivery device 20 that can be an injector or an inhalator, usually has an elongated tubular body 20 of varied shapes with a longitudinal axis A. FIG. 1A illustrates schematically an injector 20 of a pen-type having a housing 21 with a proximal end 25 and a distal end 26. The housing 21 encloses all the components of the injector 20.

Figure 3A:
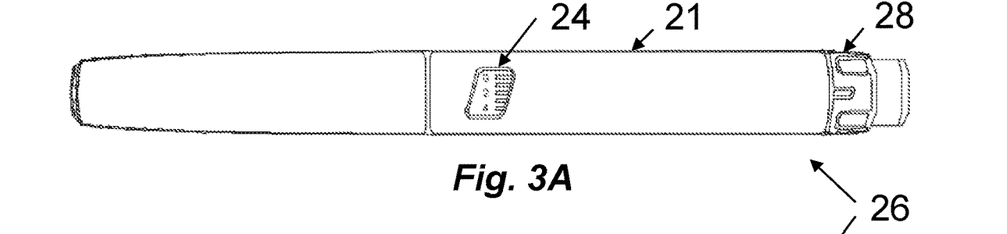
FIG. 3A-3D illustrate schematically a dosage setting mechanism, for example for a pen-injector.

The proximal end 25 of the housing 21 is provided with a needle 27 (as shown in FIG. 3A) or an inhalator nozzle (not shown) for a medicament delivery. The needle 27 is usually closed by a protecting cap (not shown).

Figure 3B:
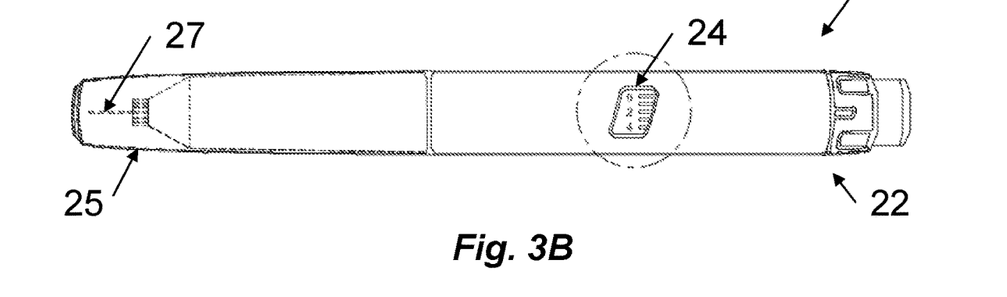
Figure 3C:
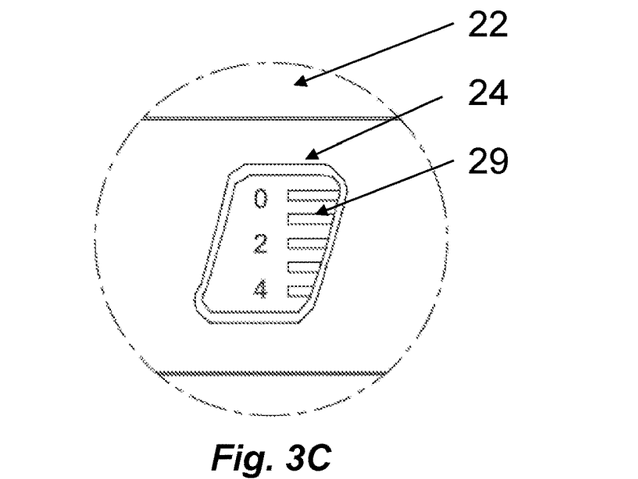
Figure 3D:
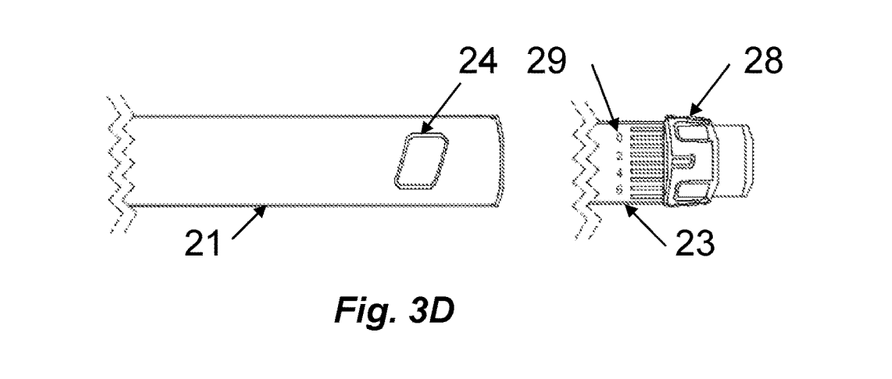

A dosage setting mechanism 22 in this embodiment is provided on the distal end 26 of the injector 20 and maybe of any conventional type dosage setting mechanisms. The dosage setting mechanism 22 here, for example, comprises a knob 28 for a manual setting of a dosage value 29 by its rotation about the axis A. The knob 28 is connected to or made as one unit with a dosage indicator 23, for example a dosage setting drum 23, as illustrated schematically in FIG. 3D. The dosage indicator 23 is provided with a plurality of dosage value indications 29 in form of digits and/or linear or tick marks on its circumferential surface. The dosage indicator 23 is surrounded by the housing 21 of the injector 20. The housing 21 has on its outer circumferential surface a dosage window or a dosage opening 24 for displaying the dosage value indications 29 or the dosage value linear, point or ticks marks 29. The opening 24 might have different shapes and might be situated at the different locations on the housing 21 as also illustrated in FIG. 3A and FIG. 3B.

The optical system 10 for a supplemental device 30 allows the user a direct monitoring of the dosage value indications 29 displayed through the monitoring opening 24 during the dosage setting process for the medicament delivery device 20. At the same time, the optical system 10 is able to receive and transmit the same optical signal or a reflected image corresponding to the displayed chosen dosage value indication 29. The optical system 10 is also able to transmit an output signal, for example, either to the supplemental device 30 or to an external remote device 40 for processing, recording and displaying the dosage value 29 on a display.

The first embodiment of the optical system 10 as illustrated in FIG. 1A is situated adjacent to the opening 24 so as to capture an optical image of the dosage value indication 29 made on the dosage indicator 23 and visible through the dosage monitoring opening 24 in the housing 21. The optical system 10 can be used with a surrounding light illuminating the dosage indicator 23 and the opening 24. Alternatively, it might be provided with a separate light source 16 enabling to use the optical system 10 in a darkness. The optical system 10 as illustrated in FIG. 1A comprises an optical sensor 11 that is, for example, a camera 11 taking the optical pictures of the dosage values 29 displayed consequently into the dosage opening 24 and an optical element 12 which is a half-silvered mirror 12.

The camera 11 might be provided with a focusing lens and usually has dimensions of about 6×6×6 mm. Alternatively, it might be the camera 11 without a focusing lens, with dimensions of about 3.2×2.9×2.1 mm.

Alternatively, the optical sensor 11 might be an optical sensor able to transform the optical image or optical signal into an electrical signal. Alternatively, the optical sensor 11 might be of a mouse type sensor able to measure a distance between two positions of the dose indicator 23 such as the dose drum, when it rotates during the dosage setting or any other suitable component for this application. The optical axis B for receiving optical signals or images of the optical sensor 11 is situated generally parallel to the medicament delivery device 20 longitudinal axis A which is also an axis for the dose drum indicator 23. The manual dosage setting process for the medicament delivery device 20 is started when the knob 28 connected to the dosage drum or dosage indicator 23 is rotated. Due to, for example, a thread connection between the dosage indicator 23 outer surface and the inner surface of the housing 21, the dosage indicator or the drum 23 is able move axially when setting the different dosage values 29. The dosage values 29 are made on the dosage indicator 23 surface and to be displayed into the dosage opening 24.

The optical sensor 11 is situated adjacently on a first side of the dosage opening 24. The optical element 12 such as a half-silvered mirror 12 is situated on the opposite side of the dosage opening 24. The half-silvered mirrors are known as a sheet of glass or plastic with a transparently thin coating of metal, now usually aluminum deposited from aluminum vapor. The thickness of the deposit is controlled so that part (typically half) of the light which is incident at a 45-degree angle and not absorbed by the coating is transmitted, and the remainder is reflected. Therefore, when the dosage value indication 29 in the dosage opening 24 is illuminated, the optical signal of the dosage value indication 29 reflected from the dosage indicator 23 due to a transparent property of the mirror 12 will partly pass through it and allow the user to monitor the dosage value 29 image on the dose indicator 23 directly while setting the dose. A partly reflected dosage value 29 optical signal changes its path due to the reflection from the mirror 12 and is transmitted to the camera 11 along its optical axis B, allowing the camera 11 take a picture of the exposed dosage value indication 29 or any other type of the optical sensor 11 (not shown here) to receive the optical signal.

Figure 1B:
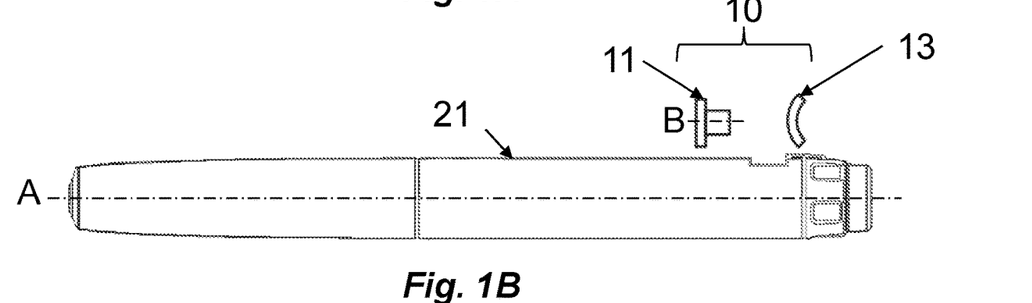
FIG. 1B illustrates a second embodiment of the optical system, where a reflected optical signal corresponding a dosage value is transmitted by a convex mirror to a camera as an optical sensor.

The second embodiment of the optical system 10 as in FIG. 1B is similarly located on the distal end of the housing 21 of the medicament delivery device 20, but instead of the half-silvered mirror 12, a convex mirror 13 is used to receive a reflected from the dose indicator 23 optical signal and reflect the dosage value 29 image signals by changing the signal transmitting direction along the optical axis B towards the camera 11 or the other suitable optical sensor 11.

Figure 1C:
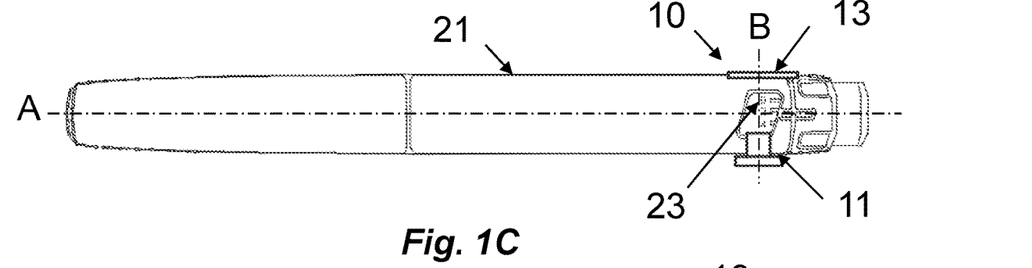
FIG. 1C is a third embodiment which is a further modification of the second embodiment of the optical system, where the convex mirror and the camera having the common optical axis B are situated not co-axially to the medicament delivery device longitudinal axis A, but so that the optical axis B is situated orthogonally to the medicament delivery device axis A. The optical system components are placed on two different opposite sides of the dosage monitoring opening.

The third embodiment of the optical system 10 as illustrated in FIG. 1C is a modification of the second embodiment of the optical system 10 using the same components such as the camera 11 and the convex mirror 13 which are situated differently on the distal end of the housing 21. These optical components 11, 13 are placed adjacently to the opposite sides of the dosage monition opening 24. The optical axis B for receiving optical signals or images by the camera 11 is situated generally orthogonally to the medicament delivery device 20 longitudinal axis A. The convex mirror 13 receives the reflected optical images of the dosage value indication 29 from the surface of the dosage indicator 23 and refracts those toward the camera 11 by changing a direction of the reflected optical signal.

Figure 1D:
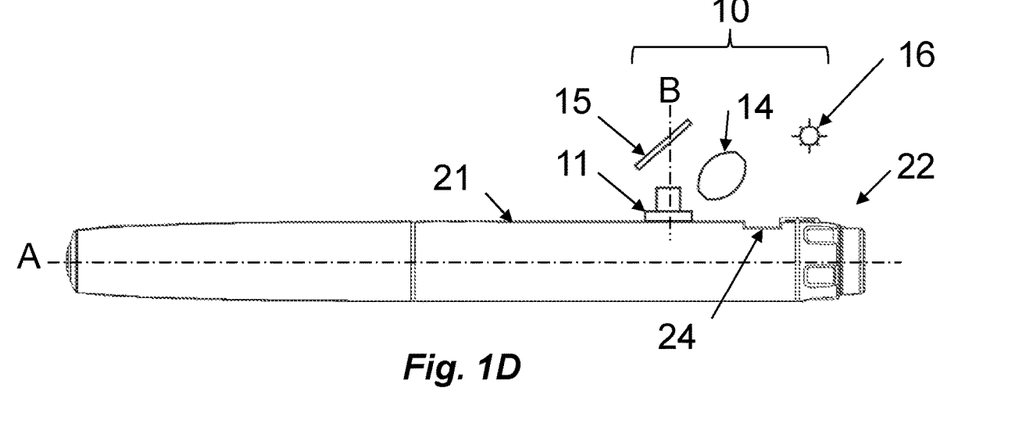
FIG. 1D is a fourth embodiment of the optical system, where a reflected optical signal corresponding a dosage value is receipted and transmitted by a convex lens and reflected via a mirror to a camera as an optical sensor

The forth embodiment of the optical system 10 as in FIG. 1D located on the distal end 26 of the medicament delivery device housing 21, where the dosage setting mechanism 22 is arranged. The optical system 10 comprises a convex lens 14, a mirror 15 and the optical sensor 11, which here is the camera 11. All those optical components 11, 14, 15 are situated adjacently to and on the same side of the dosage monitoring opening 24.

The dosage value 29 image reflected as the optical signal from the dosage indicator 23 is received by the lens 14, refracted and transmitted to the mirror 15, which reflects the dosage value 29 image signal changing its direction so as to align with the optical axis B of the camera 11.

In the fourth embodiment of the optical system 10, the optical axis B of the optical sensor 11 is situated orthogonally to the longitudinal axis A of the medicament delivery device 20. To enable the usage of the optical system in darkness, optionally a separate light source can be provided. Alternatively, the light source might be integrated in the optical sensor 11, e.g. as a flash or the like.

The optical system 10 as explained above enables to provide the optical signal of the reflected dosage value 29 image for processing and/or recording without shielding the dosage opening 24 for the observation. This is achieved by changing the optical signal's direction of transmission due to the light splitting, refraction and reflection by the optical elements 12, 13, 13, 14 and 15 of the optical system 10.

The optical system 10 might be integrated in an accessory such as a supplemental device 30 which is designed to be used together with the medicament delivery device 20. The accessory or the supplemental device 30 is intended to provide additional functionality to the user such as a recording the medicament delivery data e.g. the chosen medicament dosage value, the time of the medicament delivery and the number of the delivery in case of multiple deliveries, the medicament name, frequency etc. and the medicament delivery data possible transmission to external devices 40 such as a mobile phone, a computer or a remote server such as a cloud etc.

Additionally, it might have a relative big display 38 which makes easer to observe with the corresponding medicament delivery information, for example, the dosage, the amount of the medicament which is left and other. The display 38 may also provide to the user the other desired data such as a date, time, might have a reminder function, etc.

The different working modes of the supplemental device 30 will be disclosed later.

The supplemental device 30 may have different dimensions and ways of assembling onto the medicament delivery device 20.

The supplemental device 30 has a housing 31 with a front surface 31A and a rear surface 31B. The housing 31 might have flexible clips or arms on its rear surface 31B to be fixed around the housing 21 of the medicament delivery device 20 or affixed to its surface. Alternatively, the one of the housings 21 and 31 can have extensions and the other housing can have the corresponding accommodating the extensions grooves on their surfaces for a slide kind of connection, e.g. with a dovetail connection (not shown) or a threated interconnection.

The supplemental device 30 might be mounted and/or affixed to the medicament delivery device 20 in any conventionally known way but preferably requiring the less efforts/movements from the user, e.g. such as a snap-fit connection by at least one or alternatively two flexible mounting elements (not shown) on the backwards facing rear surface 31B of the housing 31, which is opposite to the frontal surface 31A with a transparent monitoring window 36. The flexible mounting element might have a shape corresponding to and able to enclose the medicament delivery device housing 21 outer shape in a corresponding specified area for the affixing the supplemental device 30 to it so as the dosage opening 24 and the transparent monitoring window 36 are situated one the opposite the other. The flexible mounting element e.g. in a form of flexible arms (not illustrated) of the desired shape is able to flex out at mounting so that firmly connect the supplemental device 30 and the medicament delivery device 20 to each other. Any mounting technology known in the art can be used and therefore, is not illustrated or discussed here.

Figure 2A:
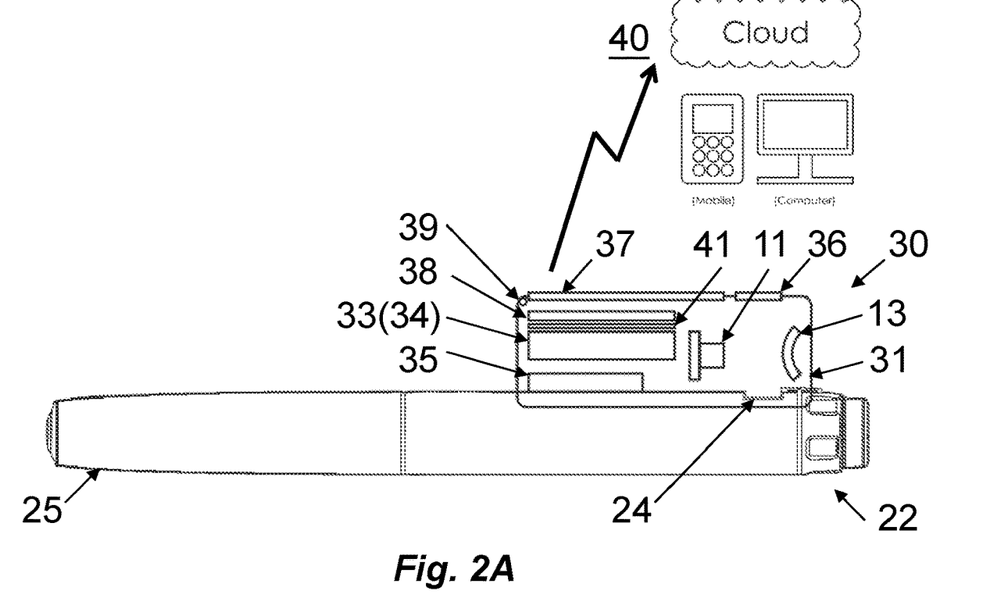
FIG. 2A illustrates a first embodiment of a supplemental device to be used together with and affixed to a medicament delivery device such as e.g. a pen-injector or an inhalator.
Figure 2B:
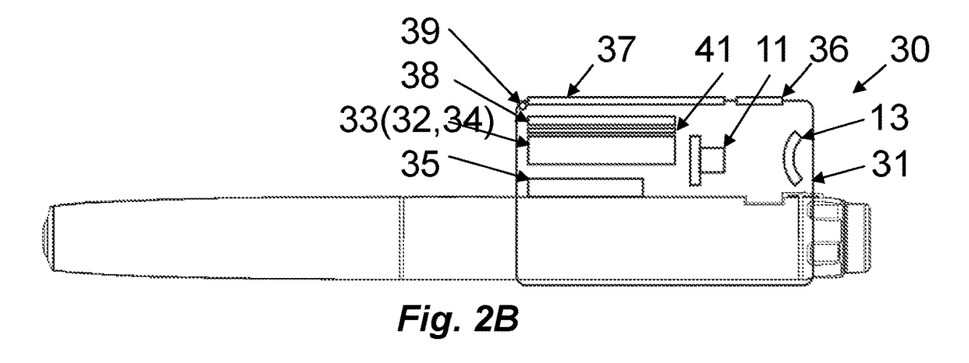
FIG. 2B illustrates a second embodiment of a supplemental device to be used together with a medicament delivery device such as a pen-injector, where the pen-injector is inserted into the supplemental device housing.
Figure 2C:
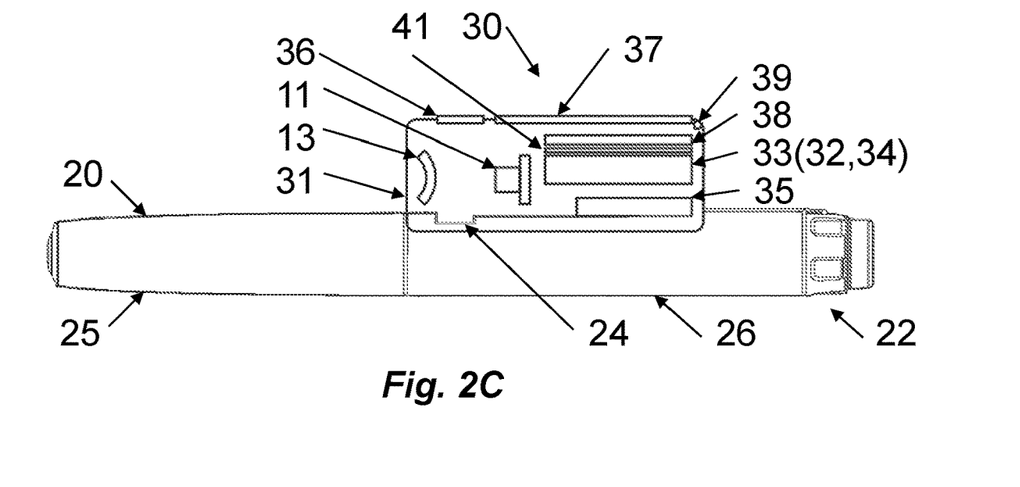
FIG. 2C illustrates a further embodiment of an assembly of a supplemental device to and a medicament delivery device such as a pen-injector.

The mounting of the supplemental device 30 on one side of the medicament delivery device 20 is schematically illustrated in FIGS. 2A and 2C. Alternatively, it might be adapted for insertion of the medicament delivery device 20 as illustrated in FIG. 2B.

The housing 31 might be done of any suitable material and can be entirely or partly transparent, if preferred. At least a part of the housing's front surface 31A is made transparent or a transparent monitoring window 36 is arranged in the housing 31. The transparent monitoring window 36 of the housing 31 shall be situated just opposite to a location of the dosage monitoring opening 24 on the medicament delivery device 20, when the supplemental device 30 is mounted onto the medicament delivery device 20 or the medicament delivery device 20 is inserted into supplemental device 30 so that to allow the user monitoring of the dosage setting and to see the chosen medicament dose value 29 displayed into the dosage opening 24 through the transparent monitoring window 36.

The supplemental device 30 can be provided with a touch panel 37 on its front surface 31A for starting the device 30 as an alternative to a start button (not shown). Alternatively, the touch panel 37 can be integrated with a display 38, e.g. a crystal display. Furthermore, an indicator 39 for example in form of a LED lamp able to change a colour depending on the supplemental device 30 or the medicament delivery device 20 status, e.g. from red to yellow and green, is provided visibly on the housing 31. A battery 35 serves as a power supply for all components of the supplemental device 30. Alternatively, if the display 38 that requires a lot of power is omitted, then the dimension and weight of the supplemental device 30 can be substantially reduced. A processing unit 33 is arranged to receive the medicament delivery dosage value as an optical or electrical signal from the optical sensor 11 for processing, analysing, recording and optionally transmitting further. The supplemental device 30 might have a memory unit 34 as a separate element or as an integrated unit in the processing unit 33.

Alternatively, the supplemental device 30 might be adapted for insertion and affixing of the medicament delivery device 20 into the housing 31 in a predetermined position so that the dosage opening 24 and the transparent monitoring window 36 are situated the opposite each another by any conventional methods. The placement of the supplemental device 30 may vary depending on a location of the dosage opening 24 location as illustrated in FIGS. 2A and 2C. The modification illustrated in FIG. 2B allows to have a connection to an external charging unit for re-charting the battery 35.

The processing unit 33 of the supplemental device 30 might be programmed in the different ways and might have different working modes depending of the user needs. The different software or algorithms to control the supplemental device 30 function can be used and the supplemental device 30 can function in a number of different modes.

Figure 4:
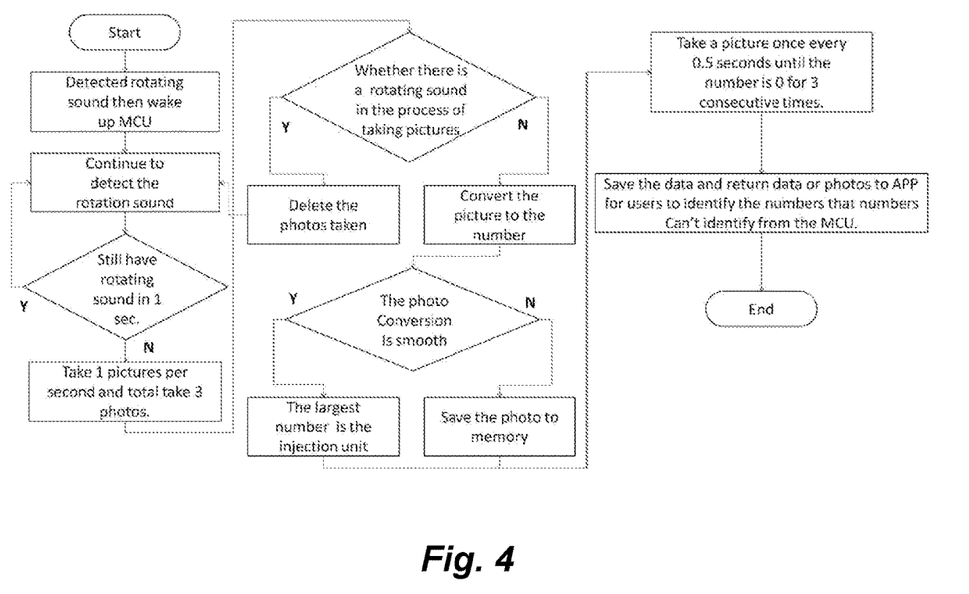
FIG. 4 illustrates a first process of a dosage setting by the supplemental device according to a first mode.

In a first mode schematically illustrated in FIG. 4, the supplemental device 30 activates from a stand-by state when the sound sensor 32 detects a sound of rotation or movement of any parts of the dosage setting mechanism 22 and activates the processing unit 33. As long as the sound sensor 32 detects the dosage setting mechanism 22 movement sounds, e.g. the sound of rotation of the dosage drum 23, all photo images taken by the optical sensor 11 (in this case, the camera 11 in the optical system as described previously) are deleted. As soon as the sound sensor 32 during e.g. one second detects no more movement sounds, the optical sensor 11 takes three photos. If during this time any sound signal appears, which means that the user still changes the dosage, the photo images are deleted and the signal is sent to continue the process. If during taking three photo images would be no movement sounds detected, which means that the user set the dosage, the taken optical images from the optical sensor 11, e.g. the camera, is converted into a digital signal corresponding the received dosage image signal. If a conversion of the image into the signal went smoothly, the signal is transmitted to the processing unit 33 for analysing the data and taking the largest number as a set dosage and saving the photos in the memory 34. If the conversion of the image is not successful, the image is saved into the memory 34. Alternatively this image might be evaluated by the user. The sound sensor 32 might be one of a microphone, an accelerometer and a vibration sensor or any other suitable conventional sensor and can be combined with the processing unit 33.

To insure accuracy of the signal, the optical sensor 11 takes photos more often, e.g. each 0.5 sec further three photos/optical images is taken so that ensure that the value is not changing until the number will be "zero" change for the three consecutive occasions (so to say, indicating that the dosage indicator 23 is not moving any longer), and after that, the processing unit 33 saves the data and may display it on the supplemental device 30 display 38 or alternatively to transmit as APP in form of the digital signal to other mobile device having own display via Bluetooth connection. Then, the first mode of the setting and recording the dosage and its delivery is finished. Afterwards, the device 30 is reset by e.g. a reset button (not shown).

Thus, a method of collecting and recording medicament dosage information from a medicament delivery device 20 comprises the following steps. A dosage setting of the medicament delivery device is started by manually operating the dose setting mechanism, e.g. by rotating a dose indicator 23. A sound or vibrations generated from the dose setting mechanism 22, is detected by a sound or a vibration sensor. The dose indicator 23 can be a dose drum or a band. The output from the sound sensor activates a processing unit 33. The sound is continuously monitored by the sound sensor until at least one sound signal per second is detected. An optical sensor, e.g. a camera is taking a number of photos at a rate of one photo per second, and deleting the photo or optical images if the sound sensor registers sound while taking the photo images. If not any sound is registered while taking the photo images, the processing unit 33 converts the taken photos or optical images into a number or a digit if the photos of a good quality, the registered number is recorded and the dosage value. If the photos of a bad quality, the photos are stored and later is sent to the user (e.g. via APP) so that the user might identify the dosage value watching photos. The largest number or digit 29 is registered as a set dosage value and the photo/optical images is stored in the memory unit 34.

The photo/optical images are taken at least twice per second, the photo/optical images are compared until the number zero is registered unchanged for three consecutive occasions. Then this data is saved in a memory 34 and the medicament delivery is ended and the supplemental device 30 is automatically put in standby mode until next usage.

Figure 5:
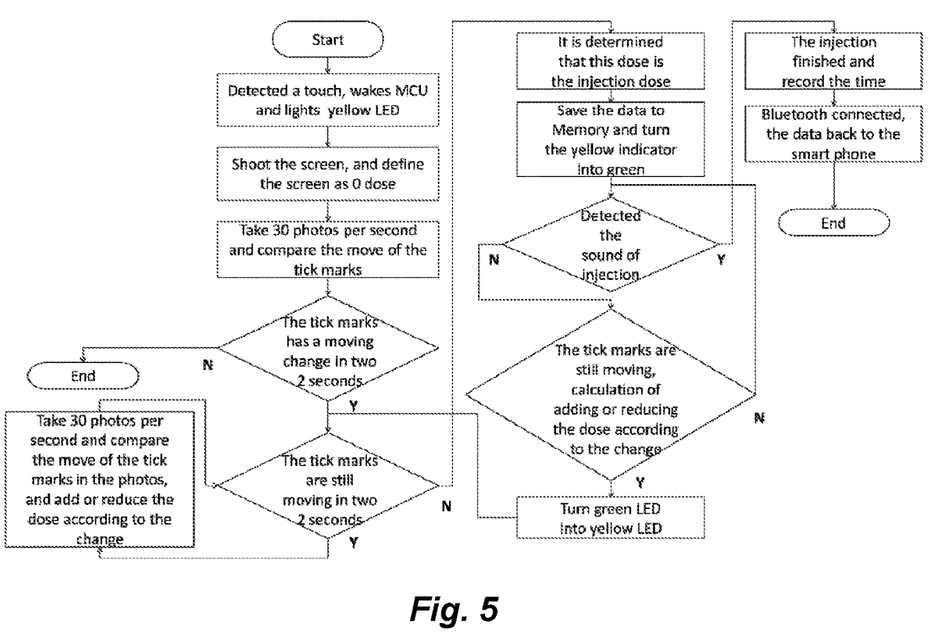
FIG. 5 illustrates a second process of a dosage setting by the supplemental device according to a second mode.

A second working mode of the supplemental device 30 is schematically illustrated in FIG. 5 and enable to detect the dosage setting based not only on optical images of the provided digit marks but also on the line, point or tick marks 29 (as in FIG. 3C) that might provide a more precise the dosage setting and allowing adjustment of the chosen dose. Besides that, the advantage of recognition by the optical system 10 the other kind of dosage value marks 29 than the digits is that those ticks or lines marks are much smaller than the digits and it can be placed many more such ticks/lines marks than the digits on the dosage indicator 23 of the same dimension. Due to the relative small dimension of the dosage indicator 23 and the required relative big size of the dosage value digits 29 on it to make the digits 29 visible, it can be a difficulty to set an exact dose if chosen dose is between the given digits 29.

The supplemental device 30 having the touch panel 37 might be activated by the user touching the panel 37 or alternatively by a start button (not shown). The processing unit 33 is now activated and turns the yellow LED light on the front surface 31A as an optical signal for the user. This mode allows to use the optical sensor 11 mostly for obtaining the optical signals of the changes of the lines/ticks marks 29 and partially of the number/digits marks 29 and use the sound sensor 32 in order to adjust up or down the chosen dosage, thus using the optical 11 and the sound 32 sensors as the signal inputs. The actual dosage value displayed into the dosage opening 24 is refracted and reflected to the optical sensor 11 as previously had been explained. The optical sensor 11 (e.g. the camera 11) takes of about thirty photos per second and the processing unit 33 compares the changes in the line marks 29 patters/positions and analyses the change so as to decide whether to increase or decrease the dose. The sound sensor 32 or alternatively a vibration sensor 32 might be used for adjusting the dose up or down depending on the amount of the detected movement/rotational sounds or the vibrations from the dosage setting mechanism 22. If the dose, for instance, does not changed during two second, the supplemental device 30 determines that the dose is set and will change the LED colour lamp from yellow to green indicating that the medicament delivery device 20 is ready for the medicament delivery. If the sensor 32 detects a sound of a medicament delivery (the injection or the inhaling), it records the time and dose and when/if necessary, transmits the medicament delivery data to a backup device via wireless connection, for instance, via Bluetooth. If the sensor 32 does not detect the sound of the medicament delivery, it turns the green LED light to the yellow one as the dosage is not set and is changing and return the algorithm to detect movement of tick/line marks during two seconds and taking 30 photos per second, analysing the marks change. When the medicament delivery device 20 is re-set and the dosage indication is became "zero", the supplemental device 30 might change the indicator 39 colour in order to indicate that the device 20 might be used again if/when it is for a multiple use.

It is to be understood that the choice of the example colours of the indicator 39 as described here is only exemplary and might be different for the different needs and embodiments.

A method of measurement and determinations of a set dosage for a medicament delivery device 20 comprises the following steps. A processor unit 33 is started by one of a touch sensor, a touch panel 37 or a sound sensor 32, the started process unit 33 lights the yellow light LED on an indicator 39. A zero dose is defined on a screen. At least 30 photo images is taken per second by an optical sensor 11 that might be a camera of the optical system as disclosed above. A change of a dosage mark 29 displayed in a dosage opening 24 of the medicament delivery device housing 21 is detected and compared those images by a processing unit 33 so as to define the movement of the marks 29. If the marks are not moving for at least two second, the dosage setting is ended. A processor unit 33 analyses if the marks 29 are still moving next two seconds, and if "yes", the camera 11 takes next 30 photo images for comparing the marks 29 movement and increase or reduce the dosage accordingly. If the mark 29 is not moving, the marks 29 determine the correct dosage. A medicament delivery data is saved in a memory unit 34 and turn the yellow LED signal to the green LED signal on the indicator 39. A sound accompanying the medicament delivery is detected by a sound sensor 32.

If the sound is detected, the medicament delivery such as an injection or an inhalation is finished and the data (dosage, time, etc.) is recorded in the memory unit 34. The signal or medicament delivery related data is transmitted to a backup device external device 40 such as one of a smart phone, a computer or a cloud via Bluetooth connection. The medicament delivery is ended and the LED signal on the indicator 39 is turned from green to the yellow LED signal, if the injection sound is not detected by the sound sensor, and the dosage marks 29 is still moving increasing or reducing the dosage. The supplemental device 30 is reset by a resetting button.

Figure 6:
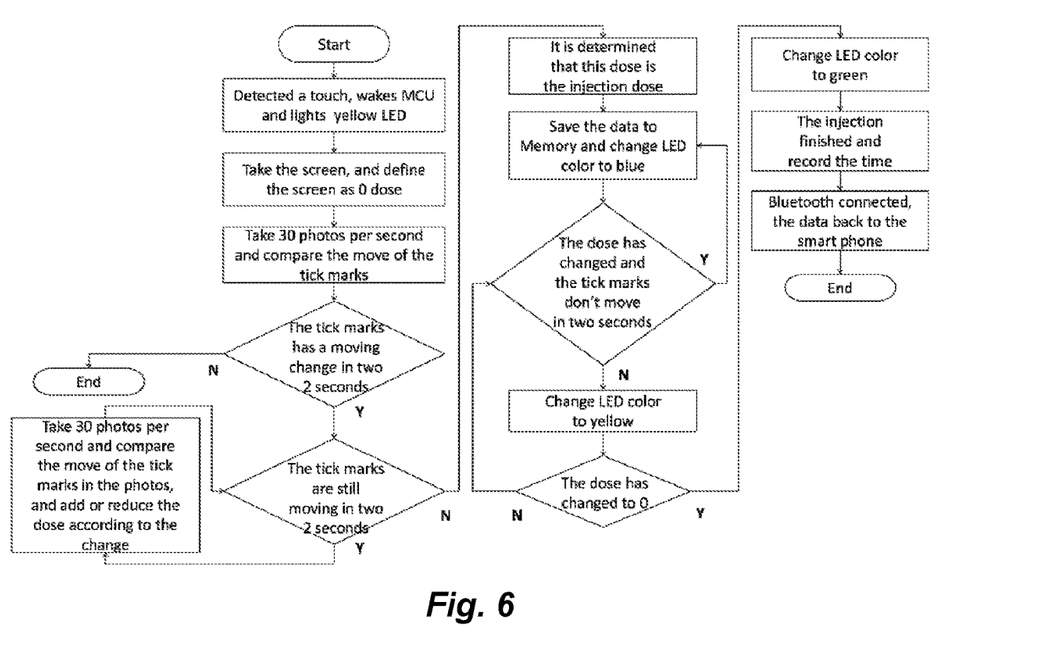
FIG. 6 illustrates a third process of a dosage setting by the supplemental device according to a third mode.

A third working mode for the supplemental device 30 is illustrated in a flow chart in FIG. 6. Similarly to the second mode, the supplemental device 30 might be started by the touch panel 37 or the start button (not shown) or a touch of the display 38 to activate the processing unit 33 and to light a yellow light on the LED indicator 39. The dosage setting mechanism 22 initial position is taken as a "zero" dose. The optical sensor 11 detects optical images of the dosage indicator 23 dosage values refracted and reflected to the sensor 11, or in case of use the camera 11, taking about 30 photos per second, comparing and analysing the tick/line marks 29 movement. The processing unit 33 compares the images 29 (or their corresponding digital signals) analysing whether or not the dosage value line marks 29 or ticks have moved or not during e.g. last 2 seconds and if not, stops analysing. If the line marks 29 continue to move, the camera 11 takes further thirty photos, compares the movement of those so as to increase/decrease the dosage according to the movement change. When the line marks 29 stop moving according to the processing unit 33 analysis, it determines the set dosage for the medicament delivery and saves this data to the memory 34 and changes the colour of the indicator 39, e.g. to the blue as the medicament delivery device 20 is being ready to be used.

In the next step, it is analysed whether the tick marks are moved or not within at least two following second. If not, that means that the user operation has changed from the setting a dose to administrating the selected dose. Then, while administrating the dose; the LED will emit yellow light.

If/when the dosage setting value 29 is changed to "zero", as being reset, the supplemental device 30 changes the LED colour of the indicator 39 to the green indicating that the medicament delivery device 20 has finished the medicament delivery and might be used again, the medicament delivery is performed successfully. The processing unit 33 records the time and the medicament delivery data in the memory unit 34. In the next optional step, the data might be transmitted via Bluetooth connection to an external device 40 such as the mobile device, e.g. a smart mobile phone or the computer, or to remote serves so called "cloud". After that, the process is finished.

It is to be understood that the foregoing is illustrative of various example embodiments and that the invention is defined only by the appended claims. A person skilled in the art will realize that the example embodiments may be modified, and that different features of the example embodiments may be combined to create embodiments other than those described herein, without departing from the scope of the present invention, as defined by the appended claims.

The invention claimed is:

1. An optical system for monitoring a dosage setting by a dosage setting mechanism for a medicament delivery device, wherein the dosage setting mechanism comprises a dose indicator with dosage value indications on a surface of the dose indicator and a dosage opening on a circumferential surface of a housing of the medicament delivery device, surrounding the dose indicator, such that the dosage value indications are displayed through the dosage opening, and wherein the optical system comprises:
   an optical sensor with an optical axis B for sensing an optical signal of the dosage value indications transmitted along the optical axis B; and
   at least one optical element for receiving the optical signal of the dosage value indications from the dosage opening for transmitting to and detecting by the optical sensor, wherein the at least one optical element changes a direction of the optical signal between the dosage opening and the optical sensor,
   wherein the optical sensor and the at least one optical element are situated on the circumferential surface of the housing of the medicament delivery device on a side of the dosage opening so that to leave the dosage opening free for enabling a user to view the dosage value indications displayed on the dosage indicator through the dosage opening.

2. The optical system according to claim 1,
   wherein the at least one optical element is one of a half-silvered mirror, a convex mirror and a combination of a convex lens and a mirror.

3. The optical system according to claim 2,
   wherein the optical sensor has the optical axis B positioned orthogonally to a longitudinal axis A of the elongated medicament delivery device; the optical sensor is spaced adjacent to the dosage opening of the medicament delivery device on a first side of the dosage opening and the convex mirror is situated on a second side of the dosage opening so that a reflected optical signal from the dosage opening is received by the convex mirror and transmitted to the optical sensor along its optical axis B.

4. The optical system according to claim 2,
   wherein the optical sensor has the optical axis B positioned orthogonally to a longitudinal axis A of the elongated medicament delivery device; the optical sensor, the mirror and the convex lens are situated on the same side of the dosage opening so that the reflected optical signal from the dosage opening is received by the convex lens and transmitted via the mirror to the optical sensor.

5. The optical system according to claim 1, wherein the optical sensor is one of a camera, a mouse sensor and a combination of a camera and a lens.

6. The optical system according to claim 5, wherein the optical sensor is one of the optical sensor able to transform the optical signal into an electrical signal, the mouse sensor able to measure a distance between two positions of the dose indicator when setting a dosage value creating a signal and an optical camera able to take photos of digits and line marks on the dose indicator corresponding to the dosage value indications displayed through the dosage opening providing optical signals: wherein the optical sensor is able to transmit the received signals for processing, analyzing and storage.

7. The optical system according to claim 1, wherein the at least one optical system further comprises a light source for illuminating the dosage value indications displayed by the dose indicator in the dosage opening.

8. The optical system according to claim 1, wherein a longitudinal axis A of the medicament delivery device and the optical axis B of the optical sensor positioned co-axially, the optical sensor is spaced adjacent to the dosage opening of the medicament delivery device on a first side of the dosage opening and the at least one the optical element is spaced on an opposite side of the dosage opening so that a reflected optical signal from the dosage opening is received by the optical element and transmitted to the optical sensor along its optical axis B.

9. A supplemental device comprising a housing and the optical system according to claim 1, wherein the supplemental device to be used with the medicament delivery device for collecting and recording dosage data from the medicament delivery device having the dosage setting mechanism and the dosage opening situated on the circumferential surface of the housing of the medicament delivery device, the supplemental device further comprising:
a sound sensor detecting a sound from the dose setting mechanism;
a processing unit for processing an output signal from the optical sensor; the sound sensor is adapted to activate the processing unit when the dosage setting starts;
a battery as a power supply,
a transparent monitoring window in the housing of the supplemental device enabling a user to view the dosage value indications displayed in the dosage opening of the housing of the medicament delivery device.

10. The supplemental device according to claim 9, further comprising
one of an optical display for displaying the medicament delivery dosage data transmitted from the processing unit, the dosage data been received from the dosage setting mechanism of the medicament delivery device by the optical sensor, transmitted to and processed by the process unit, the optical display is situated visibly on the supplemental device housing and leaving free space for the transparent monitoring window; a touch panel for activating the processing unit and displaying the dosage value and a combination of the optical display and the touch panel.

11. The supplemental device according to claim 9, wherein the supplemental device housing is adapted to be firmly and releasably attached to the medicament delivery device housing so as to the transparent monitoring window of the supplemental device housing is to be situated opposite the dosage opening of the medicament delivery device housing when the housings been assembled together.

12. The supplemental device according to claim 9, wherein the supplemental device housing is adapted for releasably receiving the medicament delivery device housing at least partially to be inserted in the supplemental device housing so that the dosage opening of the medicament delivery device housing is situated opposite to the transparent monitoring window of the supplemental device housing.

13. The supplemental device according to claim 9, wherein the sound sensor detecting the sound from the dose setting mechanism is one of a microphone, an accelerometer and a vibration sensor.

14. The supplemental device according to claim 9, wherein the supplemental device further comprising a communication module for communicating and transmitting the dosage data to an external device.

15. The supplemental device according to claim 14, wherein the external device is one of a mobile device such as a mobile phone, a computer and a remote server such as a cloud of recording, storage and monitoring of medicament delivery data.

16. The supplemental device according to claim 9, wherein the supplemental device further comprising a separate memory unit.

17. A medicament delivery device having a housing and a dosage setting mechanism with a dose indicator, wherein the dose indicator having dosage value indications on a surface of the dose indicator, and a dosage monitoring opening situated on a circumference surface of the housing of the medicament delivery device enclosing the dose indicator so that the dosage value indications on the surface of the dose indicator are visible through the dosage monitoring opening in the housing of the medicament delivery device, wherein the medicament delivery device comprises the optical system according to claim 1, which is able to receive and transmit an optical image signal from the dosage indicator visible through the dosage monitoring opening to another device for processing, recording and storage.

* * * * *